United States Patent
Hünig et al.

(10) Patent No.: US 8,586,386 B2
(45) Date of Patent: Nov. 19, 2013

(54) PEPTIDE OR PROTEIN COMPRISING A C'-D LOOP OF THE CD28 RECEPTOR FAMILY

(75) Inventors: Thomas Hünig, Wuerzburg (DE); Fred Lühder, Wuerzburg (DE); Thomas Hanke, Wuerzburg (DE)

(73) Assignee: Tegenero AG, Wuerzburg (DE)

( * ) Notice: Subject to any disclaimer, the term of this patent is extended or adjusted under 35 U.S.C. 154(b) by 0 days.

(21) Appl. No.: 12/578,558

(22) Filed: Oct. 13, 2009

(65) Prior Publication Data

US 2011/0052587 A1  Mar. 3, 2011

Related U.S. Application Data

(63) Continuation of application No. 11/581,933, filed on Oct. 17, 2006, now abandoned, which is a continuation of application No. 10/310,674, filed on Dec. 4, 2002, now abandoned.

(30) Foreign Application Priority Data

Dec. 4, 2001 (DE) .................................. 101 60 516
Jan. 10, 2002 (DE) .................................. 102 00 714

(51) Int. Cl.
*G01N 33/543* (2006.01)
*C07K 14/00* (2006.01)

(52) U.S. Cl.
USPC .......................................... 436/518; 530/350

(58) Field of Classification Search
None
See application file for complete search history.

(56) References Cited

U.S. PATENT DOCUMENTS 5,521,288 A * 5/1996 Linsley et al. ............. 530/387.3
6,090,914 A * 7/2000 Linsley et al. ................ 530/350

OTHER PUBLICATIONS

Greenwald et al., Annu. Rev. Biochem. 2005, 23: 515-548.*
Huang Z., Pharmacology and Therapeutics, 2000, 86: 201-215.*
Kawarabayashi et al., DNA Research, 1999, 6: 83-101.*
Sequence alignment, 2011, one page.*

* cited by examiner

*Primary Examiner* — Ilia Ouspenski
(74) *Attorney, Agent, or Firm* — Ann Wieczorek; Mayer & Williams PC

(57) ABSTRACT

The invention relates to a protein or peptide comprising the C'-D loop of a member of the CD28 family, uses thereof and mAbs obtainable therefrom.

3 Claims, 15 Drawing Sheets

Figure 1:
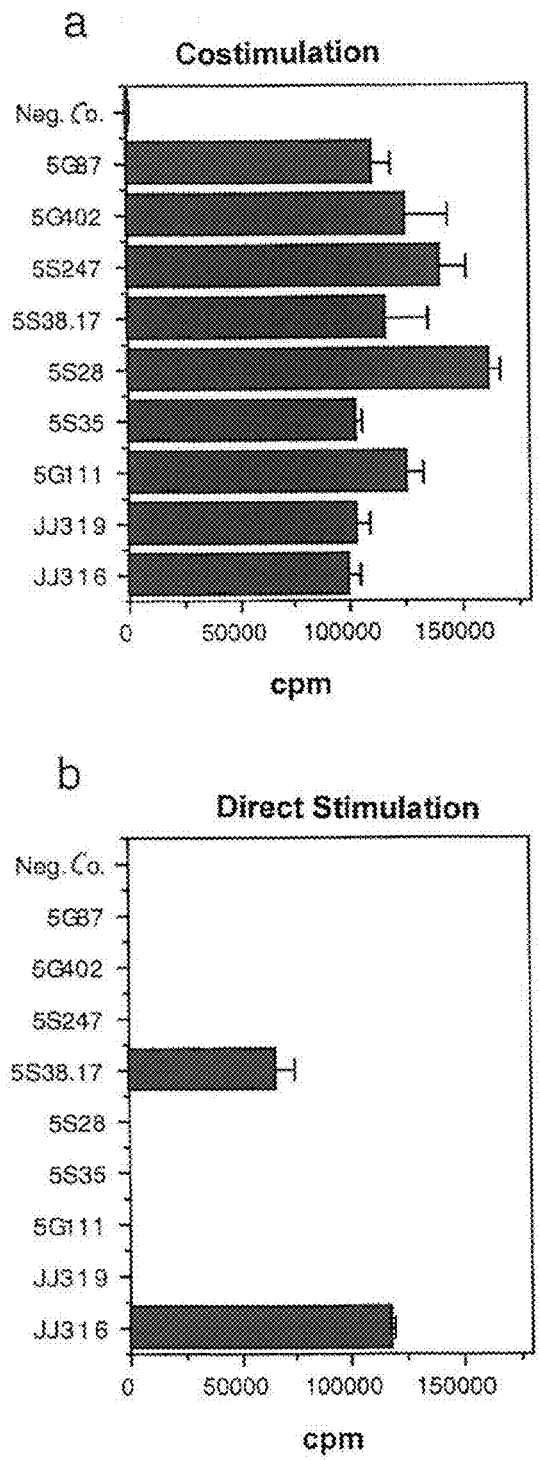

Species Differences for the extracellular Part of CD28

☐ = Mouse
▨ = Rat

JJ316    JJ319 m/r CD28
1-37 r/m CD28
1-37 m/r CD28
1-66 m CD28
A64V,E65G m CD28
S62P, A64V,
E65G

Binding of anti-human-CD28 mab to a mCD28 mutant

FIG. 7a

|  | | 10 | 20 | 30 |
|---|---|---|---|---|
| Leader-Peptid | | | | |
| Human CD28 | | MLRLLLALNLFPSIQVTGNK | AYDNAVN-LS | CKYSYNLFSR |
| Human CTLA-4 | MACLGFQRHKAQLNLATRTWPCTLLFFLFIPVFCKA | MHVAQPAVVL | AS SRG IASFV | CEYASPGKAT |
| Human ICOS | | MKSGLWYFFLFCLRIKVLTGE | INGSANYEMF | CKYPD - - IVQ |
| Human PD-1 | MQIPQAPWPVVWAVLQLGWRPGWFLDSPDRPWNP | PTFFPALLVV | TEGDN-ATFT | CS FSN TS ESF |

|  | 40 | 50 | 60 | 70 | 80 | 90 |
|---|---|---|---|---|---|---|
| Human CD28 | EFRASLHKGL | -DSAV EVCVV Y | GNYSQQ LQV | YSKTG FNCDG | KLGNESVTFY | LQNLYVNQTD |
| Human CTLA-4 | EVRVTVLRQA | DSQVTEVCAA T | YMMGNELTF | LDDS-- ICTG | TSSGNQVNLT | IQGLRAMDTG |
| Human ICOS | QFKMQLLKGG | Q - - - ILCDL T | K T KGSGNTV | S IKSL KFCHS | QLSNNSVSFF | LYNLDHSHAN |
| Human PD-1 | VLNWYRMSPS | N - - - - - -QTD K | L AAFPEDRSQ | PGQ DC KFRVT | QLPNGRDFHMS | VVRARRNDSG |

|  | 100 | 110 | 120 | 130 | 140 | 150 |
|---|---|---|---|---|---|---|
| Human CD28 | IYFCKIEVMY | PPPYLDNEKS | NGTIIIIVKGK | HLCPSPLFPG | PS--KPFWVL | VVVGGVLACY |
| Human CTLA-4 | LYICKVELMY | PPPYY-LGIG | NGTQIYVDP | EPCPDSDFLL | WILAAVSSGL | FFYSFLLTAV |
| Human ICOS | YYFCNLSIFD | PPPFKVTLT- | -GGYLIIIYES | QLCCQLKFWL | PIGCAAFVVV | CILGCILICW |
| Human PD-1 | TYLCGAISLA | PKAQIKESLR | AELRVTERRA | EVPTAHPSPSP | RPAGQFQTLV | VGVVGGLLGS |

FIG. 7b

```
                    160          170          180          190          200
Human CD28     SLLVTVAFII   FWVRSKRSRL   LHSDYMNMTP   RRPGPTRKHY   QPYAPPRDFA  AYRS
Human CTLA-4   SL           -KMLKKRSPL   TTGVYVKMPP   TEPECE-KQF   QPYFIPIN
Human ICOS                  -LTKKKYSSS   VHDPNGEYMF   MRAVNTAKKS   R---LTDVT L
Human PD-1     LVLLVWVLA    VICSRAARGTI  GARRTGQPLK   EDPSAVPVFSV  DYGELDFQWREKTPEPP Human PD-1     VPCVPEQTEYATIVFPSGMGTSSPARRGSADGPRSAQPLRPEDGHCSWPL
``` a b

FIG. 9

```
gatatccaga cgacacagac tacatcctcc cgttctgcct ctctgggaga
cagagtcacc    60 atcagttgca gggcaggtca ggacattagt aattatttaa actggtatca
gcagaaacca   120 gatggaactg ttaagctcct gatctactac acatcaagat tacactcagg
agtcccatca   180 aggttcagtg gcagtgggtc tggaacagat tattctctca ccattagcaa
cctggagcaa   240 gaagatattg ccacttactt ttgccaacag ggtcatacgc ttccgtggac
gttcggtgga   300 ggcaccaagc tggaaatcaa a
             321
``` a

```
1                                                    50
 DIQTTQTTSS LSASLGDRVT ISCRAGQDIS NYLNWYQQKP DGTVKLLIYY 51                                                  100
 TSRLHSGVPS RFSGSGSGTD YSLTISNLEQ EDIATYFCQQ GHTLPWTFGG 101   107
   GTKLEIK
``` b

FIG. 9

```
gatgtgcagc ttcaggagtc gggacctggc ctggtgaaac cttctcagtc
tctgtccctc    60 acctgcactg tcactggcta ctcaatcacc agtgattatg cctggaactg
gatccggcag    120 tttccaggaa acaaactgga gtggatgggc tacataagat acagtggtag
tactagctac    180 aatccatctc tcaaaagtcg aatctctatc actcgagaca catccaagaa
ccagttcttc    240 ctgcagttga attctgtgac tactgaggac acagccacat attactgtgc
aagagattgg    300 ccgcgaccga gctactggta cttcgatgtc tggggcgcag ggaccacggt
caccgtctcc    360 tca
``` c

```
1                                                  50
DVQLQESGPG LVKPSQSLSL TCTVTGYSIT SDYAWNWIRQ FPGNKLEWMG 51                                                 100
YIRYSGSTSY NPSLKSRISI TRDTSKNQFF LQLNSVTTED TATYYCARDW 101        121
PRPSYWYFDV WGAGTTVTVS S
``` d

FIG. 9 caggtccaac tgcagcagtc cggacctgag ctggtgaagc cggggacttc
agtgaggatt      60 tcctgcgagg cttctggcta caccttcaca agctactata tacactgggt
gaaacagagg     120 cctggacagg gacttgagtg gattggatgt atttatcctg gaaatgtcaa
tactaactat     180 aatgagaagt tcaaggacaa ggccacactg attgtagaca catcctccaa
cactgcctac     240 atgcagctca gcagaatgac ctctgaggac tctgcggtct atttctgtac
aagatcacac     300 tacggcctcg actggaactt cgatgtctgg ggcgcaggga ccacggtcac
cgtctcctca     360 e 1                                                        50
 QVQLQQSGPE LVKPGTSVRI SCEASGYTFT SYYIHWVKQR PGQGLEWIGC 51                                                       100
 IYPGNVNTNY NEKFKDKATL IVDTSSNTAY MQLSRMTSED SAVYFCTRSH 101           120
 YGLDWNFDVW GAGTTVTVSS f

FIG. 9

```
gacatccaga tgaaccagtc tccatccagt ctgtctgcat cccttggaga
cacaattacc    60 atcacttgcc atgccagtca aacatttat gtttggttaa actggtacca
gcagaaacca    120 ggaaatattc ctaaactctt gatctataag cttccaacc tgcacacagg
cgtcccatca    180 aggtttagtg gcagtggatc tggaacaggc ttcacattaa ccatcagcag
cctgcagcct    240 gaagacattg ccacttacta ctgtcaacag ggtcaaactt atccgtacac
gttcggaggg    300 gggaccaagc tggaaataaa a
              321
``` g

```
1                                                    50
  DIQMNQSPSS LSASLGDTIT ITCHASQNIY VWLNWYQQKP GNIPKLLIYK 51                                                  100
  ASNLHTGVPS RFSGSGSGTG FTLTISSLQP EDIATYYCQQ GQTYPYTFGG 101   107
  GTKLEIK
``` h

File Name : humanised VLC 5.11

```
1                                                                15
Asp Ile Gln Met Thr Gln Ser Pro Ser Ser Leu Ser Ala Ser Val 16                                                               30
Gly Asp Arg Val Thr Ile Thr Cys His Ala Ser Gln Asn Ile Tyr 31                                                               45
Val Trp Leu Asn Trp Tyr Gln Gln Lys Pro Gly Lys Ala Pro Lys 46                                                               60
Leu Leu Ile Tyr Lys Ala Ser Asn Leu His Thr Gly Val Pro Ser 61                                                               75
Arg Phe Ser Gly Ser Gly Ser Gly Thr Asp Phe Thr Leu Thr Ile 76                                                               90
Ser Ser Leu Gln Pro Glu Asp Phe Ala Thr Tyr Tyr Cys Gln Gln 91                                                              105
Gly Gln Thr Tyr Pro Tyr Thr Phe Gly Gly Gly Thr Lys Val Glu 106 107
Ile Lys
```

FIG 10a

File Name : humanised VHC 5.11

```
1                                                               15
Gln Val Gln Leu Val Gln Ser Gly Ala Glu Val Lys Lys Pro Gly 16                                                              30
Ala Ser Val Lys Val Ser Cys Lys Ala Ser Gly Tyr Thr Phe Thr 31                                                              45
Ser Tyr Tyr Ile His Trp Val Arg Gln Ala Pro Gly Gln Gly Leu 46                                                              60
Glu Trp Ile Gly Cys Ile Tyr Pro Gly Asn Val Asn Thr Asn Tyr 51                                                              75
Asn Glu Lys Phe Lys Asp Arg Ala Thr Leu Thr Val Asp Thr Ser 76                                                              90
Ile Ser Thr Ala Tyr Met Glu Leu Ser Arg Leu Arg Ser Asp Asp 91                                                              105
Thr Ala Val Tyr Phe Cys Thr Arg Ser His Tyr Gly Leu Asp Trp 106                                                             120
Asn Phe Asp Val Trp Gly Gln Gly Thr Thr Val Thr Val Ser Ser
```

FIG 10b

US 8,586,386 B2

PEPTIDE OR PROTEIN COMPRISING A C'-D LOOP OF THE CD28 RECEPTOR FAMILY

STATEMENT OF RELATED APPLICATIONS

This application is a continuation of U.S. patent application Ser. No. 11/581,933, filed Oct. 17, 2006, entitled "Peptide Or Protein Containing A C'-D Loop Of The CD28 Receptor Family,", which is a continuation of U.S. patent application Ser. No. 10/310,674, filed Dec. 4, 2002, entitled "Peptide or Protein Containing A C'-D Loop Of The CD28 Receptor Family," now abandoned. Each of the prior applications is incorporated herein by reference in its entirety.

FIELD OF THE INVENTION

The invention relates to a protein or peptide containing a partial sequence of a member of the CD28 receptor family, a nucleic acid coding for such a peptide, a plasmid containing such a nucleic acid, hybridoma cells forming monoclonal antibodies (mAbs) binding to such a peptide, mAbs obtainable from such hybridoma cells, and methods of use of the peptide and the mAbs.

DEFINITIONS

Monoclonal antibodies are antibodies being produced by hybrid cell lines (so-called hybridomas) typically resulting from the fusion of a B cell of animal or human origin producing antibodies with a suitable myeloma tumor cell.

The amino acid sequence of human CD28 is known under the accession no. NM_006139.

The amino acid sequence of human CTLA-4 is known under the accession no. L15006.

The amino acid sequence of human ICOS is known under the accession no. AJ277832.

The amino acid sequence of human PD-1 is known under the accession no. U64863.

The C'-D loop of CD28 comprises the amino acids 52 to 66 of the above CD28 sequence (numbering according to FIG. 7, see also Ostrov, D. A. et al.; Science (2000), 290:816-819). The term C'-D loop will in the following also comprise any partial sequences thereof.

A loop or a binding site arranged therein is freely accessible, if there is for a defined binding partner no steric hindrance for the binding site in the loop by the sequences or molecules outside of the loop.

Activation of T lymphocytes is the increase of metabolic activity, increase of the cell volume, synthesis of immunologically important molecules and initiation of the cell division (proliferation) of T lymphocytes as a response to an external stimulation. Inhibition is the opposite process. For example are such processes caused by occupation of the CD28 molecule on T cells by special CD28-specific monoclonal antibodies. The activation of the T lymphocytes with the described side effects is part of the physiologic immune reaction, in pathologic situations however there may be lost control thereof (lympho-proliferative diseases), or may be insufficient (immunodeficiency).

Modulation of the proliferation of T cells is either the increase of the activity (for a pathologically insufficient activation) or reduction or inhibition of the activity (for pathologically lympho-proliferative diseases).

Several sub-groups of the T cells means at least sub-groups of CD4 and CD8 T cells expressing CD 28.

An analogous peptide is a peptide the amino acid sequence of which differs from that one of the peptide to which it is analogous, which binds however a defined binding partner with at least the same affinity. Deviations in the sequence may be deletions, substitutions, insertions and elongations. An analogous peptide will usually comprise a tertiary (partial) structure and/or exposition being very similar to the peptide, in a (cell surface) protein, and otherwise only needs to comprise or form a binding site for the defined binding partner in the section analogous to the immediate binding section of the peptide.

A mimicry compound of a mAb is a natural or synthetic chemical structure behaving in a binding assay as a defined mAb mimicrying the mimicry compound.

A mimicry compound of a C'-D loop is a natural or synthetic chemical structure to which specifically bind mAbs being superagonistic and specific for a member of the CD28 family.

The term mAbs comprises, in addition to structures of the usual Fab/Fc constructions, also structures consisting of or comprising the Fab fragment only. It is also possible to exclusively use the variable region, the fragment of the heavy chains being connected in a suitable manner, for instance also by means of synthetic bridge molecules, with the fragment of the light chain, in such a way that the binding regions of the chains form the antibody binding site. The term antibody also comprises (complete) chimeric and humanized antibodies.

Superagonistic modulation of the proliferation of T cells means that no costimulation, i.e. no further binding event in addition to a binding of a mAb or of a mimicry compound to a member of the CD28 family is required for the stimulation or inhibition of the proliferation.

A screening method comprises the use of a target, for instance a partial sequence from CD28, one or more known or unknown substances being contacted with the target and a binding event being detected or not detected. In the case of the detection of a binding event, the substance is selected. In the case of the use of a mixture of substances, typically a deconvolution follows a selection of the mixture for the purpose of the determination of binding components in the selected mixture.

As a CD28 family is designated a group of T cell surface receptors having an immuno-regulatory activity. This may be either stimulating, as in the case of the CD28, or inhibiting, as in the case of the CTLA-4. To the CD28 family belong CD28, CTLA-4, PD-1 and ICOS.

A substrate can be soluble, insoluble and/or immobilized. A substrate can be formed of any natural or synthetic molecules, for instance of amino acid chains, among others. In this respect a protein or a peptide in the terminology of this text needs not necessarily be a protein or a peptide according to the conventional definition. Usually, however, a protein or peptide according to the terminology used herein is also a protein or peptide in the usual terminology.

BACKGROUND OF THE INVENTION AND PRIOR ART

For the understanding of the invention, first the following technological background is important. The activation of resting T cells for the proliferation and functional differentiation first requires the occupation of two surface structures, so-called receptors: i.e. of the antigen receptor having a different specificity from cell to cell and being necessary for the detection of antigens, for instance viral fission products; and of the CD28 molecule expressed in an identical manner on all resting T cells with the exception of one sub-group of the human CD8 T cells, said CD28 molecule binding in to ligands on the surface of other cells. This is called the costimulation of the antigen-specific immune reaction by CD28. In cell culture, these processes can be simulated by occupying the antigen receptor and the CD28 molecule by suitable mAbs. In the classical system of the costimulation, neither the occupation of the antigen receptor nor of the CD28 molecule alone will lead to the T cell proliferation, the occupation of both receptors is however effective. This observation has been made for T cells of man, mouse and rat.

There are known, however, also mAbs that can alone initiate the T cell proliferation. Such a superagonistic (that is independent from the occupation of the antigen receptor) activation of resting T cells has been observed in the following systems: in the document Brinkmann et al., J. Immunology, 1996, 156: 4100-4106, it has been shown that a very small fraction (5%) of human T lymphocytes carrying the surface marker CD45 RO being typical for resting T lymphocytes, is activated by the CD28-specific mAb 9.3 normally requiring costimulation with addition of the growth factor interleukin-2 (IL-2) without occupation of the antigen receptor. In the document of Siefken et al., Cellular Immunology, 1997, 176: 59-65, it has been shown that a CD28-specific mAb produced in a conventional manner, i.e. by immunization of mice with human cells, can activate in cell culture a sub-group of human T cells without occupation of the antigen receptor for the proliferation, if CD28 is occupied by this mAb and the cell-bound mAbs are in addition cross-linked with each other by further antibodies. It is common to the in this respect known antibodies that only a small fraction of the T cells can be activated.

In the document of Tacke et al., Eur. J. Immulog., 1997, 17: 239-247, two kinds of CD28-specific monoclonal antibodies with different functional properties have been described: costimulatory mAbs costimulating the activation of resting T cells with a simultaneous occupation of the antigen receptor only; and superagonistic mAbs being able to activate T lymphocytes of all classes in vitro and in animal experiments for the proliferation, without occupation of the antigen receptor. Both in this respect known mAbs originate from an immunization with cells, on the surface of which rat CD28 is expressed, and which are obtainable by different selections directed to their respective properties. Finally, from WO 98/54225 is known another superagonistic mAb, namely CMY-2.

The in this respect known superagonistic mAbs do not meet in their stimulatory effect the requirements with regard to the strength of the activating effect or the width of the activated sub-populations of T lymphocytes or do not have the required human specificity.

TECHNICAL OBJECT OF THE INVENTION

The invention is based therefore on the technical object to provide means, by use of which superagonistic compounds can be found which bind to one or several members of the CD28 family and have an improved stimulatory or inhibiting effect, as well as to specify such compounds.

The Findings the Invention is Based on

The invention is based on the examination of the binding regions of superagonistic mAbs at CD28 as well as the interaction found in these experiments of the C'-D loop of CD28 with superagonistic mAbs. Further, the invention is based on the finding that a corresponding binding region for superagonistic mAbs can be found in the other members of the CD28 family, namely there, too, the C'-D loops. From this basic findings, various aspects for technical teachings of the invention can be deducted.

BASICS OF THE INVENTION AND PREFERRED EMBODIMENTS

For achieving the technical object, the invention teaches a protein or peptide comprising the C'-D loop of a member of the CD28 family, or comprising a peptide being analogous thereto or comprising a mimicry compound thereto, not however a member of the CD28 family. In other words, the essential element of a protein or peptide according to the invention is the C'-D structure (or of an analogous/mimicry substance thereto), and that irrespective of whether and which sequences follow on both sides of the loop. It is only essential that the loop structure is sufficiently exposed, in order to offer access for superagonistic mAbs or mimicry compounds and to prevent in the case of the specific binding possibility a binding not for steric reasons. According to the invention, it is surprising that all found superagonistic CD28-specific mAbs bind to the C'-D loop, whereas the not superagonistic CD28-specific mAbs do not bind thereto. By a single group of target structures with regard to their spatial distribution on members of the CD28 family, thus prospective effective substances against a number of different diseases are made accessible.

In the embodiment of a peptide, in particular of an oligopeptide (4 to 9 amino acids) or a polypeptide (10-100 amino acids) or of a mimicry compound thereto, it is preferred that the ends thereof are each bound to a binding position of a substrate, the binding positions of the substrate being spatially arranged with regard to each other according to the binding positions for the C'-D loop, the C'-D loop or the peptide being analogous thereto or the mimicry compound thereto being fixed in a three-dimensional configuration according to the C'-D loop, the bound C'-D loop or the peptide being analogous thereto or the mimicry compound thereto being freely accessible for antibodies or mimicry compounds thereto, and the substrate not being a member of the CD28 family without a C'-D loop. Thus a three-dimensional structure permitting a binding with superagonistic substances is provided.

In detail, a peptide or protein according to the invention may comprise an amino acid sequence seq.-ID 41 (human CD28 loop), not however be human CD28, seq.-ID 42 (human CTLA-4 loop), not however be human CTLA-4, seq.-ID 43 (human ICOS loop), not however be human ICOS, or seq.-ID 44 (human PD-1 loop), not however be human PD-1. One or two amino acids may be added according to FIG. 7 to the 3' end and/or the 5' end. But partial sequences thereof may also be comprised in the peptides according to the invention, for instance according to the sequences seq.-ID 1 to 4, respectively. The seq.-ID 5 to 10 indicate variants of the human CD28 loop. The seq.-ID 12 to 17 indicate variants of the human CTLA-4 loop. The seq.-ID 19 to 24 indicate variants of the human ICOS loop. The seq.-ID 26 to 31 indicate variants of the human PD-1 loop. One or more amino acids of the sequence 11 may be added according to FIG. 7a to one of the sequences 1, 7 or 9. One or more amino acids of the sequence 18 may be added according to FIG. 7a to one of the sequences 2, 14 or 16. One or more amino acids of the sequence 25 may be added according to FIG. 7a to one of the sequences 3, 21 or 23. One or more amino acids of the sequence 32 may be added according to FIG. 7a to one of the sequences 4, 28 or 30. The above sequences are sections according to the invention, to which superagonistic mAbs will specifically bind. It can in particular be seen, when comparing the sequences, that the primary structure of the loop is specific for the respective family members. By selection of the C'-D loop of a specific member and thus by application of substances having specificity for this selected loop, thus alternatively an activation or an inhibition of the proliferation can be obtained.

A (CD28-specific) protein or peptide according to the invention or a mimicry compound thereto can be identified by that one or more prospective proteins, peptides or mimicry compounds are subjected to a binding test with e.g. one of the mAbs 9D7 or 5.11A, and binding peptides are selected. The mentioned mAbs are new superagonistic CD28-specific mAbs, which are described in detail in the experimental section hereof. By means of corresponding mAbs with specificity for a C'-D loop of another CD28 family member, proteins, peptides or mimicry compounds according to the invention and being specific for the other members can be identified. Such corresponding mAbs may be obtained in an analogous manner.

The invention further relates to a nucleic acid coding for a peptide according to the invention or for a protein comprising such a peptide, not however coding for a member of the CD28 family, and to a vector, e.g. plasmid, comprising such a nucleic acid, operably linked to a suitable promotor.

The peptide, protein according to the invention or a mimicry compound thereto according to the invention can be used in a method for producing mAbs which superagonistically modulate the proliferation of T cells of several to all sub-groups, a non-human mammal being immunized with the protein or peptide or the mimicry compound thereto, from the non-human mammal cells being taken, hybridoma cells being produced from the cells, and such obtained hybridoma cells being selected, the culture supernatant of which contains mAbs, which bind to the C'-D loop of the protein or peptide or the mimicry compound thereto, such hybridoma cells and mAbs obtainable with such hybridoma cells. Human mAbs according to the invention can alternatively however also be produced by that B lymphocytes are selected which bind to the loop, and that their expressed immunoglobulin genes are cloned. Furthermore, human mAbs can be isolated from phage libraries. The average man skilled in the art is without any problems in a position, using his knowledge, to execute such alternative methods, so that no detailed description is needed here.

By using the invention, new superagonistic CD28 family specific mAbs and/or mimicry compounds can however also be identified. Therefore the invention also relates to the use of a peptide, of a protein according to the invention or of a mimicry compound thereto according to the invention in a screening method for the identification of substances superagonistically modulating the proliferation of T cells of several to all sub-groups, a prospective substance or a mixture of prospective substances being subjected to a binding assay with the peptide or protein or mimikry compound thereto, and substances binding to the peptide or protein or mimikry compound thereto being selected. In principle, any conventional binding assay can be used. Of special importance may be here the search for mimicry compounds, since these are typically so-called small molecules having pharmacological advantages over macro-molecules. In such a screening method for mimicry compounds, a substance library can be screened with high throughput. Both aforementioned uses may be carried out with a native CD 28 receptor family member as well.

A peptide, protein or mimicry compound thereto according to the invention as well as the mAbs or mimicry compounds thereto according to the invention have therapeutic relevance, since thereby lymphoproliferative diseases may be treated by inhibition of the proliferation, as well as immunodeficiency diseases by activation of the proliferation. The induction of effector functions, e.g. secretion of effector substances, is also possible. This is achieved by selection or design of the mAb or of the mimicry compound according to a specificity and high affinity for a specific member of the CD28 family. If a higher specificity/affinity is desirable, for instance, for controlling surprising side effects, the process may be such that a second ligand in addition to the mAb or the mimicry compound with specificity for the special family member is searched, and the second ligand is linked, after an analysis of the relative spatial positions of the bound two ligands with respect to each other, by a bridging molecule with the mAb or the mimicry compound. The determination of the position of two ligands with respect to each other after binding to a target can for instance be made by X-ray structure analysis or multi-dimensional NMR correlation spectroscopy, for instance $^{15}N/^{1}H$ NMR. A second ligand can be determined by conventional screening methods, the special CD28 family member being used as a target. It is understood that the second ligand does not bind at the C'-D loop, but spaced thereto. On the other hand it is possible that a peptide, protein or mimicry compound according to the invention thereto hot having an otherwise physiological effect, competitively binds natural ligands of the members of the CD28 family, and thus creates a reverse effect by prevention of a pathologically caused natural activation or inhibition.

Therefore the invention relates on one hand also to the use of a peptide, protein or mimicry compound thereto according to the invention for producing a pharmaceutical composition for the modulation of the physiological T cell proliferation, wherein a such compound is optionally mixed with suitable carrier and auxiliary compounds and galenically prepared for the desired mode of administration, e.g. injection i.v or i.p.

On the other hand, therefore, the invention relates to the use of a mAb according to the invention or a mimicry compound thereto according to the invention for producing a pharmaceutical composition for the treatment of diseases with pathologically reduced CD4 T cell numbers, in particular AIDS, for producing a pharmaceutical composition for the treatment following stem cell transplantations after chemo or radio therapy of leukemic diseases, for producing a pharmaceutical composition for multiplying and/or qualitatively influencing immune reactions after vaccinations, and for producing a pharmaceutical composition for the treatment of autoimmune-inflammatory diseases. Mixing and galenic preparation is performed in an according manner.

The invention finally relates to therapeutic methods, wherein to a person suffering from a proliferative or immunodeficient disease, a pharmaceutical composition according to the invention is administered.

Figure 2:
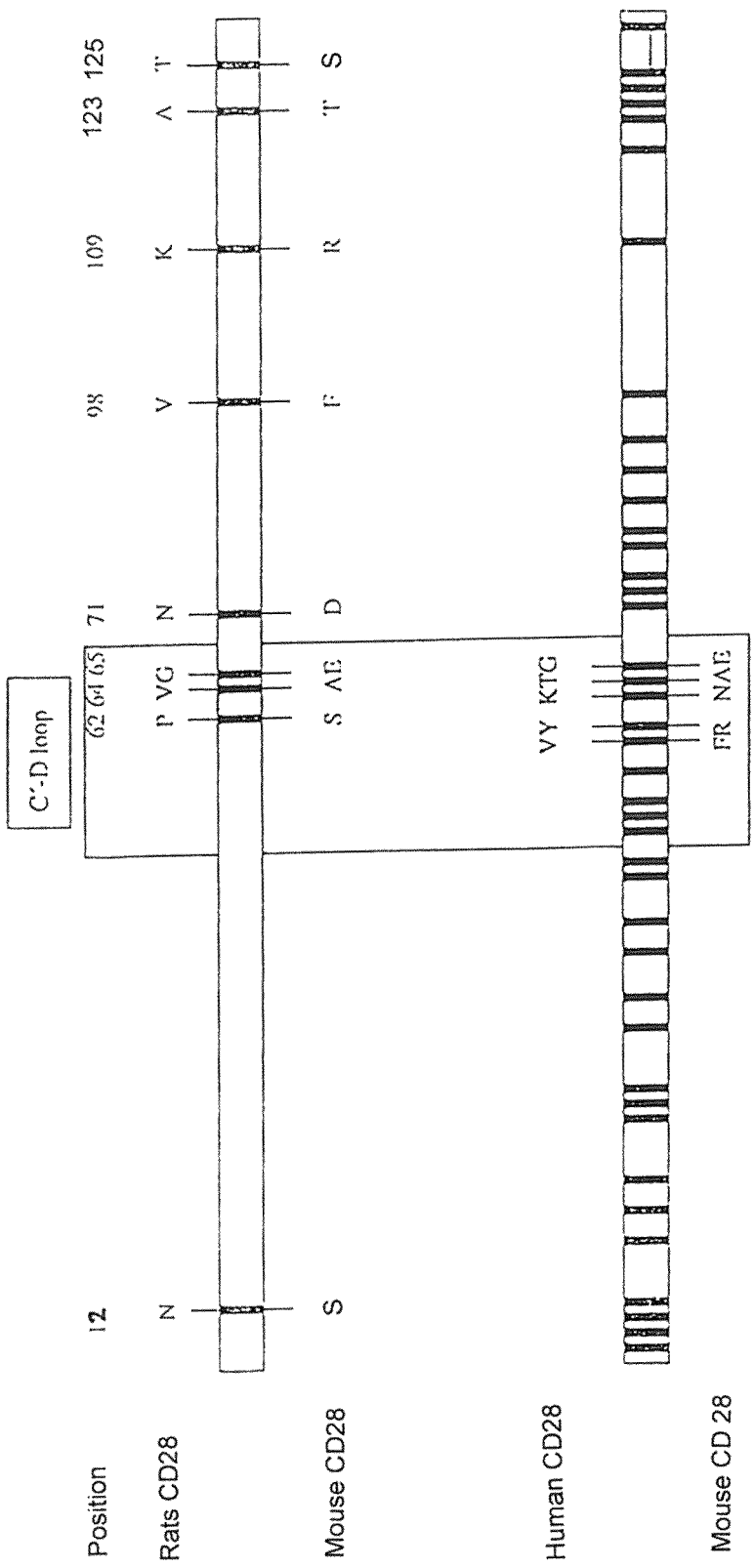
Figure 3:
Figure 3:
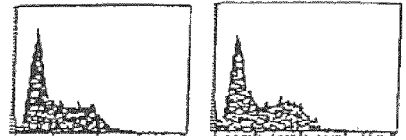
Figure 3:
Figure 3:
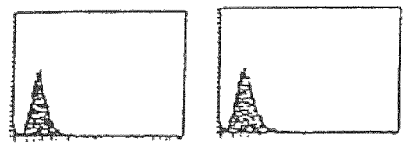
Figure 3:
Figure 3:
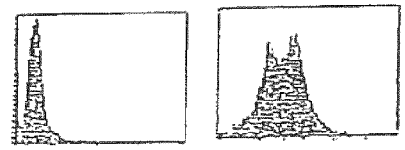
Figure 3:
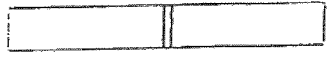
Figure 3:
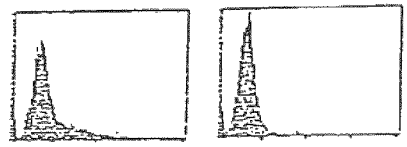
Figure 3:
Figure 3:
Figure 4:
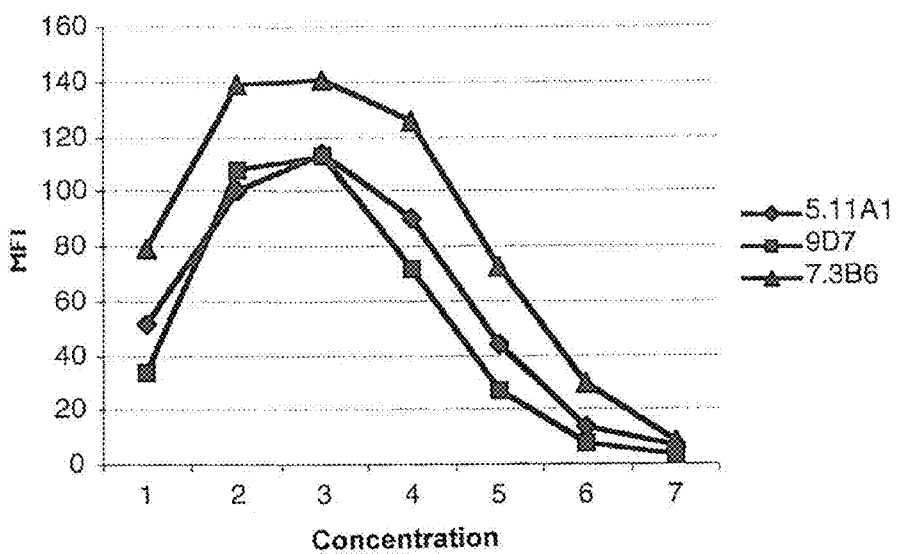
Figure 4:
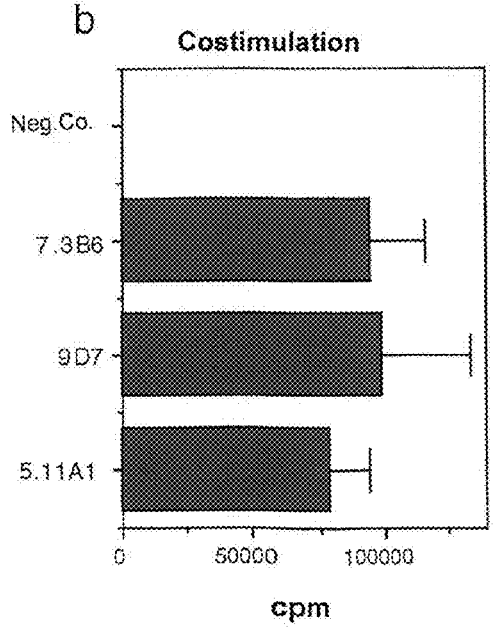
Figure 4:
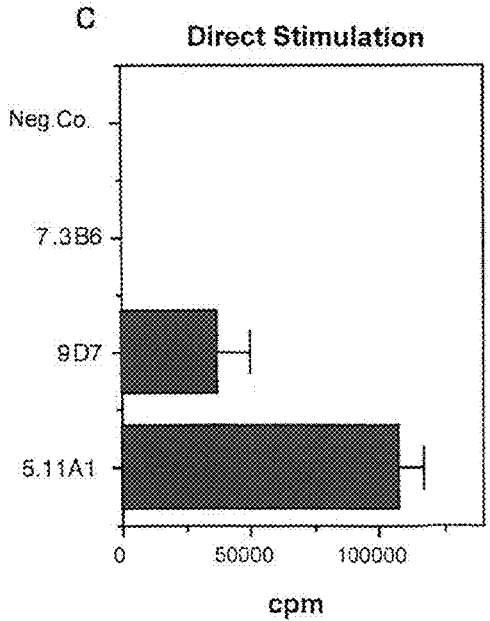
Figure 5:
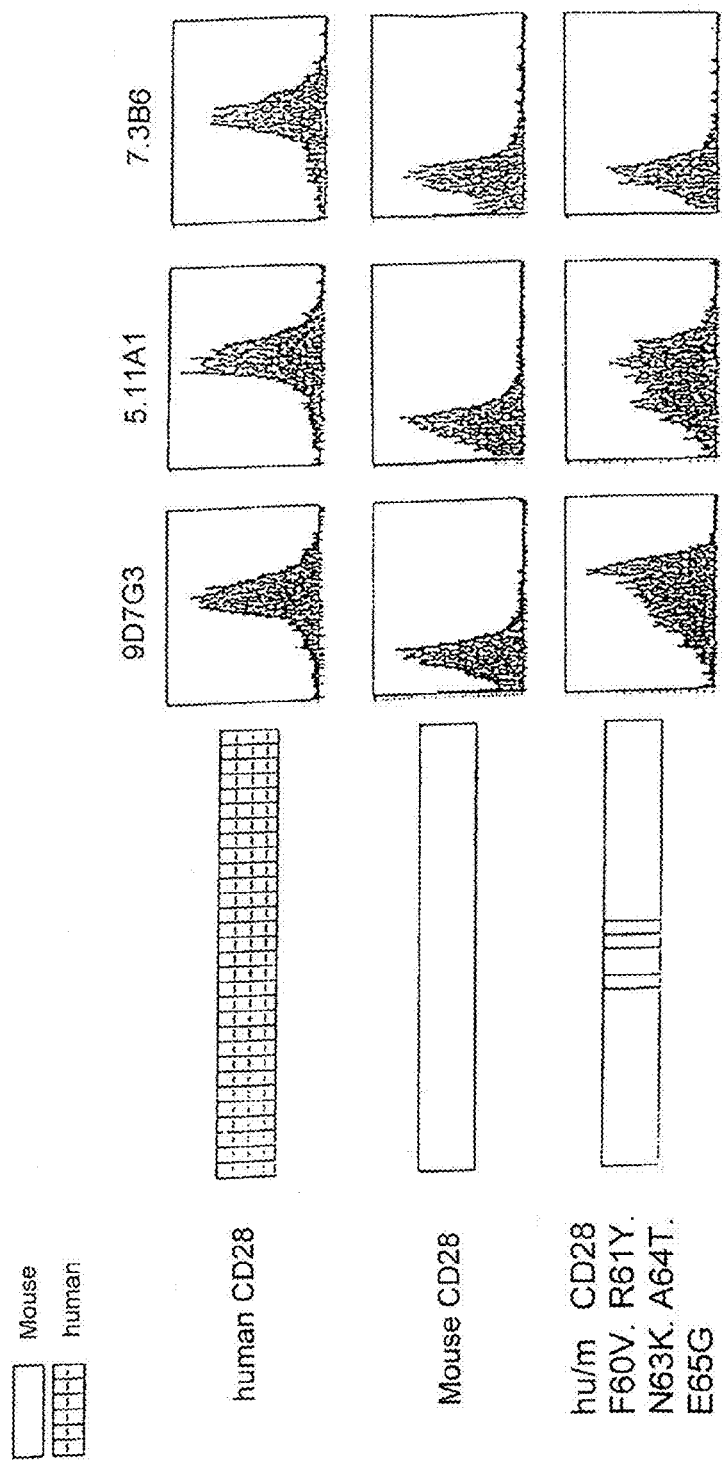
Figure 6:
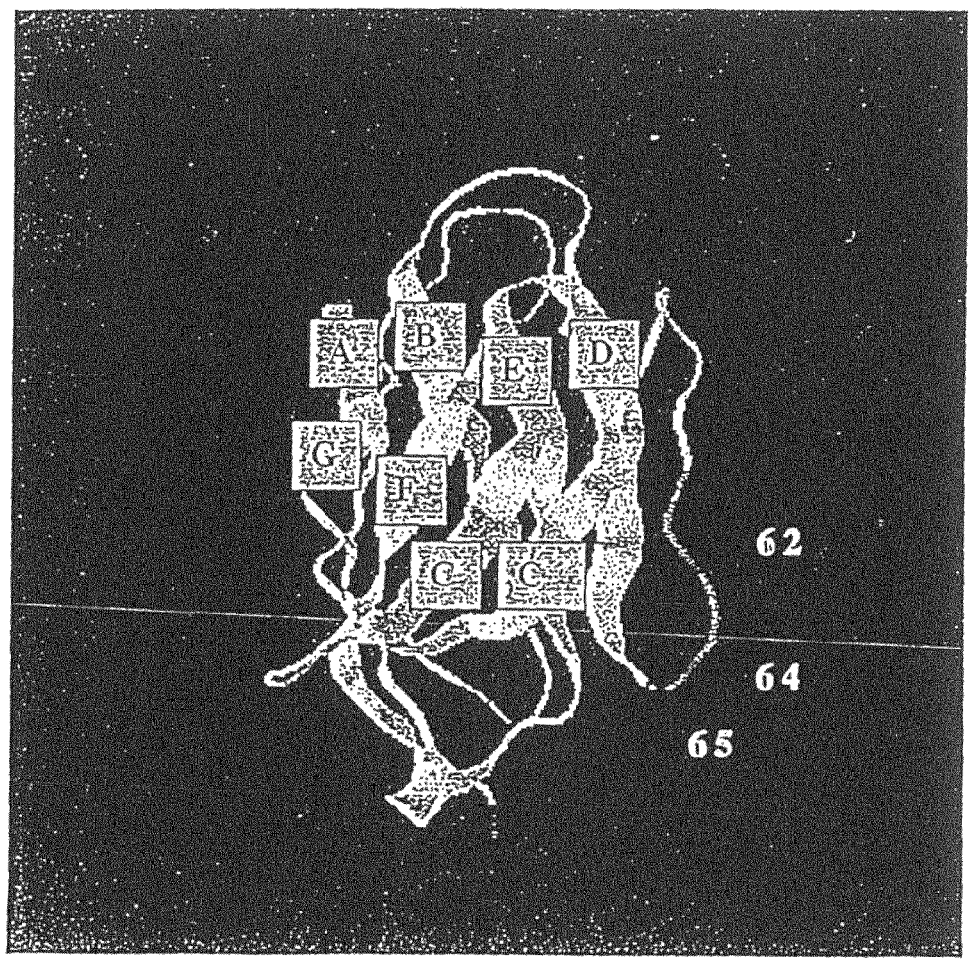

In the following, the invention is described in more detail with respect to examples representing embodiments only. There are:

FIG. 1: stimulation of T lymphocytes from the rat with various CD28-specific mAbs (a: costimulation, b: superagonistic, i.e. direct stimulation), FIG. 2: a sequence comparison between mouse, rat and human CD28 in the section of the C'-D loop (in box), FIG. 3: experimental results for the localization of the binding site of superagonistic mAbs at the CD28 molecule of the rat, FIG. 4: binding of various human CD28-specific mAbs to CD28 (a) and costimulatory (b) and superagonistic, i.e. directly stimulatory (c) activity of the mAbs of FIG. 4a, FIG. 5: binding tests that show that human CD28-specific superagonistic mAbs specifically bind to the C'-D loop, FIG. 6: a three-dimensional representation of CD28 with marking of the C'-D loop, FIGS. 7a and 7b: sequence alignment under emphasis of the C'-D loop or analogous structures, for various members of the CD28 family; Human CD28 (SEQ ID NO 45); Human CTLA (SEQ ID NO: 46); Human ICOS (SEQ ID NO: 47) and Human PD-1 (SEQ ID NO: 48).

FIGS. 8a and 8b: experiments for the activation of cells by means of human CD28-specific mAbs and mutated mouse CD28 molecules, FIG. 9: representation of the sequences seq.-ID 33-40 (a-h), and FIG. 10: humanized variable domain of the mAb 5.11A1; FIG. 10a: light chain: VLC5.11 (SEQ ID NO: 49); FIG. 10b: heavy chain: VHC5.11 (SEQ ID NO: 50).

FIG. 1 shows the stimulation of freshly isolated T lymphocytes from the rat in the form of a 3H thymidine incorporation. The approach corresponds to the one described in document WO98/54225, to which reference to a full extent is made here and in the following, and the scope of disclosure of which is hereby incorporated in the present text. In FIG. 1a is shown the costimulation, i.e. in all wells, T cell receptors (TCR) specific mAbs were bound to the plastic surface. For lack of costimulation, the negative control (uppermost row) does not show any incorporation. Costimulation is then given by the addition of CD28-specific mAbs in a soluble form. All the different CD28-specific mAbs used are shown. This series of various CD28-specific mAbs originate from an approach of the immunization and production of hybridoma cell lines described in WO98/54225 already. These are culture supernatants containing sufficient CD28-specific mAbs for a saturating binding to the 2×10$^5$ cultivated cells. From FIG. 1a can be taken that all of these mAbs are able to activate in a costimulating manner, i.e. to induce in presence of the anti-TCR mAbs the thymidine incorporation. In FIG. 1b is shown the stimulation in absence of TCR specific mAbs. This experiment has also been performed as described in document WO98/54225. It can be seen that only two mAbs are capable to stimulate the T lymphocytes in absence of a TCR signal. These mAbs have thus superagonistic activity.

Furthermore it has been examined whether costimulatory and superagonistic CD28-specific mAbs bind to different sections of the CD28 molecule. The mAbs were produced by immunization of mice with CD28 from the rat; as expected, they all do not react with mouse CD28 (not shown). Since the mAbs can thus only recognize such sections of the rat CD28 molecule which differ from that of the mouse, first a sequence comparison between CD28 from the mouse and the rat was performed (see FIG. 2, upper part). The differences between the two species are highlighted. For the designation of the amino acids, the one-letter code was used. As prototypes for a conventional rat CD28-specific mAb was used JJ319, for a superagonistic mAb JJ316 (see WO98/54225).

In FIG. 3, the mapping of the binding region is shown. Expression plasmids were constructed, wherein one part of the extracellular domain of CD28 originates from the mouse, another one from the rat. This is shown by bars or lines, respectively; on the right-hand side thereof the binding of the mAbs JJ316 and JJ319 to mouse fibroblasts (L929 cells) is represented, which have been transfected with these expression plasmids. In the first two lines of FIG. 3 (m/r and r/m 1-37), the binding of both antibodies to the "right-hand" half of the sequence is mapped: Both will bind if this originates from the rat. In the reverse construct (rm CD28 1-37, left-hand rat, right-hand mouse), there is no binding. In the third line (m/r CD28 1-66) it is shown that JJ316 does not bind anymore, whereas the still present part of the rat sequence ("right-hand") is still sufficient for a detection by JJ319. Thus, the two mAbs detect different epitopes on the CD28 molecule, and the binding of the superagonist JJ316 is located in that region which originated in the construct of the first line, not however in the construct of the third line from the rat. A clear candidate therefor is the section in the box of FIG. 2.

In lines 4 and 5 of FIG. 3, therefore first two and then three amino acids were so modified in this region of the mouse CD28 molecule that they will now represent the rat sequence. By this "transplantation" of three amino acids only, the binding capability for mAb JJ316, not however that of JJ319 could be transferred. In Table 1 the binding data for the whole group of CD28-specific mAbs are summarized. There exists a unique correlation: a significant binding to the C'-D loop of the rat which has been created by transfer of the amino acid positions 62, 64 and 65 to the CD28 molecule of the mouse, could be found for the two superagonistic mAbs JJ316 and 5S38 17 only, not however for the conventional (only costimulatory) mAbs. A costimulatory mAb (5S35) detects the epitope in the box to a very weak degree and binds very strongly to the "conventional" epitope.

The next figures deal with superagonistic human-specific mAb. These have also been produced in mice, thus do not react with the CD28 molecule of the mouse. The mice were immunized with human CD28-transfected A20/J mouse B lymphoma cells (see WO98/54225) and additionally boostered prior to the fusion with commercially available human CD28-Fc fusion protein (bought from R and D Systems). In a series of fusion experiments, 24 out of several thousand cell lines were identified which produce human CD28-specific mAbs (binding to mouse L929 cells expressing human CD28, not however to untransfected L929 cells), in an analogous manner to the screen in document WO98/54225. From these, two showed the desired superagonistic activity (9D7 and 5.11A), whereas all new mAbs have a conventional costimulatory activity. In the following, in particular these two superagonistic mAbs will be described. As an example for a conventional human CD28-specific mAb, the also newly generated mAb 7.3B6 is used.

FIG. 4a shows that the used preparations of the three new mAbs bind comparatively well and also with comparable titer to human T lymphocytes. An experiment is shown, wherein freshly isolated mononuclear cells from the human blood (so-called PBMC) were first treated with different dilution steps of the used mAbs on ice; then they were washed, and the bound mAb was made visible by a secondary antibody marked by a fluorescence dye, said secondary antibody specifically detecting the bound mouse mAbs. By using another mAb detecting human CD4 T cells, and to which a second fluorescence dye was bound, the binding of the titrated mAbs could be determined by electronic gating selectively for the CD4 T lymphocytes. By "MFI" is given the average fluorescence intensity being a measure for the amount of the bound CD28-specific mAb. The concentrations represent 3-fold dilutions of a standardized original preparation. It is fully normal that in this test the highest concentration gives a weaker signal than the following titration steps; this has to do with the avidity (bivalent binding) of mAbs and does not play any role in the context discussed here.

In FIGS. 4b and c the capability of these three new CD28-specific mAbs to stimulate—in presence and absence of a TCR signal—freshly isolated human T cells to growth is compared. Again, a 3H thymidine incorporation is shown, as described above for the rat. For FIG. 4b, the wells were coated with a mAb which reacts with the human TCR/CD3 complex. Thus, the costimulation was measured. It can be seen that the proliferation without costimulation with one the mAbs fails to appear (negative control), all three antibodies are however capable to stimulate the cell division. For FIG. 4c, the absence of a TCR/CD3-specific mAb was selected. Only the antibodies 9D7 and 5.11A could stimulate in a superagonistic way.

After the epitope for superagonistic mAb for the rat has been defined, and two new superagonistic mAbs having specificity for human CD28 have been isolated, it has been checked whether these mAbs bind to the corresponding position of the human CD28 molecule. As can be seen from FIG. 2, the CD28 molecules of mouse and man differ in numerous positions. Based on the mapping of the superagonistic epitope for the rat, it has therefore been directly checked whether the binding site for the superagonistic epitope on human CD28 to the CD28 molecule of the mouse can be achieved by "transplantation" of the five amino acids of this homologous region. The results are shown in FIG. 5. Taking into account the background of the homogeneously represented mouse sequence for the extracellular domain of the CD28 molecule (center) the exchanged (mouse to man) amino acid positions are shown as lines (bottom). The numbers at the side indicate in addition the individual positions and mutations (F60V means for instance that at position 60 the phenylalanine of the mouse has been replaced by a valine of the human sequence). Adjacent thereto, the binding of the three examined mAbs is represented. As the figure shows, all three mAbs detect human CD28, only the two mAbs 9D7 and 5.11A however react with the mouse molecule, into which the five amino acids of the human CD28 have been transplanted at the crucial position. Taking into account the great variety of differences, this specific generation of the reactivity is surprising and confirms to a full extent the findings, derived from the experiments with rat CD28, that superagonistic mAbs must bind to a specific, namely exactly this site of the molecule.

In FIG. 6 is shown a three-dimensional model of the CD28 molecule. The newly identified binding region is highlighted. It corresponds to the sequence in the box in FIG. 2. Concerning its structure, the extra-cellular domain of CD28 belongs to the so-called immunoglobulin super family being characterized by two superimposed β sheets as a basic structure. The labeling of these bands follows a pattern as given in the literature. It is important for the representation shown here that the region identified as an epitope for superagonistic CD28-specific mAbs in rat and mouse is described by "C'-D loop". It has thus been shown that mAbs having specificity for the C'-D loop of the CD28 molecule show superagonistic activity, thus can be used for the activation of T lymphocytes in the meaning of the document WO98/54225. The superagonistic activity of C'-D loop-specific mAbs in rat and man shows that therein not the sequence of the epitope, but its position or shape is important.

CD28 belongs to a family of cell surface receptors with immuno-regulatory activity. This is either stimulating (CD28, ICOS) or inhibiting (CTLA-4, PD-1). In FIG. 7, the sequences of the known members of the CD28 family are shown in the sense of an "alignment". The C'-D loop for CD28 is highlighted. Analogous loops of the other molecules (in box) are a correspondingly favorable target structure for the development of superagonistic ligands. It should be noted, with regard to FIG. 7, that "-" is a gap in the alignment, i.e. the amino acids following thereto are immediately connected to each other.

Figure 8:
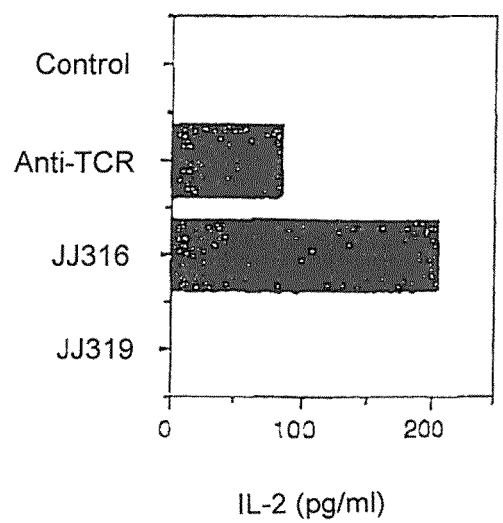
Figure 8:
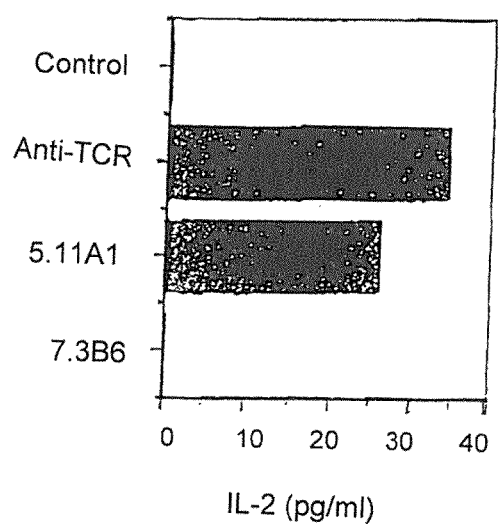

In the experiments of FIG. 8, it has been examined whether mAbs according to the invention having specificity for the C'-D loop of the rat or man do not only bind to the mouse CD28 with "transplanted" C'-D loop of the rat or man (see FIGS. 3 and 5), but whether there is really an activation. For this purpose, T tumor cells of the mouse, BW, were transfected either with the construct of FIG. 3, line 5 (rat C'-D loop transfer) or with the construct of FIG. 5, line 3 (human C'-D loop). The activation of these cells is not measured by cell division (they proliferate anyway), but by the production of the cytokine IL-2. FIG. 8 shows first that without stimulation there is no IL-2 production (negative control). The stimulation with a T cell receptor-specific mAb induces IL-2 production (positive control). FIG. 8a shows the results when using the superagonistic mAb JJ316 of the rat, whereas FIG. 8b shows the results for the human C'-D loop-specific mAb 5.11A. In either case the respective cell lines are stimulated for the IL-2 production. As expected, there is however no stimulation by "conventional" CD28-specific mAbs, since these do not only not bind to the C'-D loop, but cannot detect the construct at all, because they are specific for rat or human-specific sequences not contained in the construct.

In FIG. 9a is shown the nucleic acid sequence of the variable region of the light chain of a mAb 9D7 according to the invention (seq.-ID 33). FIG. 9b shows the peptide coded thereby (seq.-ID 34). FIG. 9c shows the nucleic acid sequence of the variable region of the heavy chain of this mAb (seq.-ID 35). FIG. 9d is the peptide coded thereby (seq.-ID 36).

In FIG. 9e is represented the nucleic acid sequence of the variable region of the heavy chain of a mAb 5.11A according to the invention (seq.-ID 37). FIG. 9f shows the peptide coded thereby (seq.-ID 38). FIG. 9g shows the nucleic acid sequence of the variable region of the light chain of this mAb (seq.-ID 39). FIG. 9h shows the peptide coded thereby (seq.-ID 40). FIG. 10 shows the humanized variable domain of the mAb 5.11A. FIG. 10a is the light chain, and FIG. 10b the heavy chain.

TABLE I

Binding of anti-rat CD28 mAbs to mouse and rat CD28 and various CD28 mutants

| mAb | Mouse CD28 | Rat CD28 | mCD28, S62P A64V, E65G | m/rCD28 Mval1269I |
|---|---|---|---|---|
| Control | − | − | − | − |
| JJ316 | − | +++ | +++ | − |
| JJ319 | − | +++ | − | +++ |
| 5S28 | − | ++ | − | ++ |
| 5S38.17 | − | +++ | +++ | − |
| 5S247 | − | +++ | − | +++ |
| 5G40/3 | − | +++ | − | +++ |
| 5G87 | − | ++ | − | ++ |
| 5G111 | − | ++ | − | ++ |
| 5G35 | − | +++ | + | +++ |

The invention claimed is:

1. A peptide consisting of a C'-D loop of CD28, which is immobilized on a substrate.

2. A peptide according to claim 1, wherein the ends thereof are bound to one binding position each of a substrate, wherein the binding positions of the substrate have the same distances from each other as compared with the distance of the ends of the peptide in naturally occurring CD28, wherein the C'-D loop is fixed in a three dimensional configuration according to the C'-D loop in CD28, the bound C'-D loop being freely accessible for antibodies.

3. A peptide or protein according to claim 1, comprising an amino acid sequence having SEQUENCE ID NO: 41, or SEQUENCE ID NOs:5-10.

* * * * *

SEQUENCE LISTING

<160> NUMBER OF SEQ ID NOS: 50

<210> SEQ ID NO 1
<211> LENGTH: 6
<212> TYPE: PRT

-continued

```
<213> ORGANISM: Artificial
<220> FEATURE:
<223> OTHER INFORMATION: Novel Sequence

<400> SEQUENCE: 1

Val Tyr Ser Lys Thr Gly
1               5

<210> SEQ ID NO 2
<211> LENGTH: 5
<212> TYPE: PRT
<213> ORGANISM: Artificial
<220> FEATURE:
<223> OTHER INFORMATION: Novel Sequence

<400> SEQUENCE: 2

Phe Leu Asp Asp Ser
1               5

<210> SEQ ID NO 3
<211> LENGTH: 6
<212> TYPE: PRT
<213> ORGANISM: Artificial
<220> FEATURE:
<223> OTHER INFORMATION: Novel Sequence

<400> SEQUENCE: 3

Val Ser Ile Lys Ser Leu
1               5

<210> SEQ ID NO 4
<211> LENGTH: 6
<212> TYPE: PRT
<213> ORGANISM: Artificial
<220> FEATURE:
<223> OTHER INFORMATION: Novel Sequence

<400> SEQUENCE: 4

Gln Pro Gly Gln Asp Cys
1               5

<210> SEQ ID NO 5
<211> LENGTH: 4
<212> TYPE: PRT
<213> ORGANISM: Artificial
<220> FEATURE:
<223> OTHER INFORMATION: Novel Sequence

<400> SEQUENCE: 5

Tyr Ser Lys Thr
1

<210> SEQ ID NO 6
<211> LENGTH: 5
<212> TYPE: PRT
<213> ORGANISM: Artificial
<220> FEATURE:
<223> OTHER INFORMATION: Novel Sequence

<400> SEQUENCE: 6

Tyr Ser Lys Thr Gly
1               5

<210> SEQ ID NO 7
<211> LENGTH: 5
<212> TYPE: PRT
<213> ORGANISM: Artificial
<220> FEATURE:
```

```
<223> OTHER INFORMATION: Novel Sequence

<400> SEQUENCE: 7

Val Tyr Ser Lys Thr
1               5

<210> SEQ ID NO 8
<211> LENGTH: 6
<212> TYPE: PRT
<213> ORGANISM: Artificial
<220> FEATURE:
<223> OTHER INFORMATION: Novel Sequence

<400> SEQUENCE: 8

Tyr Ser Lys Thr Gly Phe
1               5

<210> SEQ ID NO 9
<211> LENGTH: 7
<212> TYPE: PRT
<213> ORGANISM: Artificial
<220> FEATURE:
<223> OTHER INFORMATION: Novel Sequence

<400> SEQUENCE: 9

Val Tyr Ser Lys Thr Gly Phe
1               5

<210> SEQ ID NO 10
<211> LENGTH: 5
<212> TYPE: PRT
<213> ORGANISM: Artificial
<220> FEATURE:
<223> OTHER INFORMATION: Novel Sequence

<400> SEQUENCE: 10

Ser Lys Thr Gly Phe
1               5

<210> SEQ ID NO 11
<211> LENGTH: 8
<212> TYPE: PRT
<213> ORGANISM: Artificial
<220> FEATURE:
<223> OTHER INFORMATION: Novel Sequence

<400> SEQUENCE: 11

Gly Asn Tyr Ser Gln Gln Leu Gln
1               5

<210> SEQ ID NO 12
<211> LENGTH: 4
<212> TYPE: PRT
<213> ORGANISM: Artificial
<220> FEATURE:
<223> OTHER INFORMATION: Novel Sequence

<400> SEQUENCE: 12

Leu Asp Asp Ser
1

<210> SEQ ID NO 13
<211> LENGTH: 5
<212> TYPE: PRT
<213> ORGANISM: Artificial
<220> FEATURE:
<223> OTHER INFORMATION: Novel Sequence
```

```
<400> SEQUENCE: 13

Leu Asp Asp Ser Ile
1               5

<210> SEQ ID NO 14
<211> LENGTH: 5
<212> TYPE: PRT
<213> ORGANISM: Artificial
<220> FEATURE:
<223> OTHER INFORMATION: Novel Sequence

<400> SEQUENCE: 14

Phe Leu Asp Asp Ser
1               5

<210> SEQ ID NO 15
<211> LENGTH: 6
<212> TYPE: PRT
<213> ORGANISM: Artificial
<220> FEATURE:
<223> OTHER INFORMATION: Novel Sequence

<400> SEQUENCE: 15

Leu Asp Asp Ser Ile Cys
1               5

<210> SEQ ID NO 16
<211> LENGTH: 7
<212> TYPE: PRT
<213> ORGANISM: Artificial
<220> FEATURE:
<223> OTHER INFORMATION: Novel Sequence

<400> SEQUENCE: 16

Phe Leu Asp Asp Ser Ile Cys
1               5

<210> SEQ ID NO 17
<211> LENGTH: 5
<212> TYPE: PRT
<213> ORGANISM: Artificial
<220> FEATURE:
<223> OTHER INFORMATION: Novel Sequence

<400> SEQUENCE: 17

Asp Asp Ser Ile Cys
1               5

<210> SEQ ID NO 18
<211> LENGTH: 8
<212> TYPE: PRT
<213> ORGANISM: Artificial
<220> FEATURE:
<223> OTHER INFORMATION: Novel Sequence

<400> SEQUENCE: 18

Tyr Met Met Gly Asn Glu Leu Thr
1               5

<210> SEQ ID NO 19
<211> LENGTH: 4
<212> TYPE: PRT
<213> ORGANISM: Artificial
<220> FEATURE:
<223> OTHER INFORMATION: Novel Sequence

<400> SEQUENCE: 19
```

```
Ser Ile Lys Ser
1

<210> SEQ ID NO 20
<211> LENGTH: 5
<212> TYPE: PRT
<213> ORGANISM: Artificial
<220> FEATURE:
<223> OTHER INFORMATION: Novel Sequence

<400> SEQUENCE: 20

Ser Ile Lys Ser Leu
1               5

<210> SEQ ID NO 21
<211> LENGTH: 5
<212> TYPE: PRT
<213> ORGANISM: Artificial
<220> FEATURE:
<223> OTHER INFORMATION: Novel Sequence

<400> SEQUENCE: 21

Val Ser Ile Lys Ser
1               5

<210> SEQ ID NO 22
<211> LENGTH: 6
<212> TYPE: PRT
<213> ORGANISM: Artificial
<220> FEATURE:
<223> OTHER INFORMATION: Novel Sequence

<400> SEQUENCE: 22

Ser Ile Lys Ser Leu Lys
1               5

<210> SEQ ID NO 23
<211> LENGTH: 7
<212> TYPE: PRT
<213> ORGANISM: Artificial
<220> FEATURE:
<223> OTHER INFORMATION: Novel Sequence

<400> SEQUENCE: 23

Val Ser Ile Lys Ser Leu Lys
1               5

<210> SEQ ID NO 24
<211> LENGTH: 5
<212> TYPE: PRT
<213> ORGANISM: Artificial
<220> FEATURE:
<223> OTHER INFORMATION: Novel Sequence

<400> SEQUENCE: 24

Ile Lys Ser Leu Lys
1               5

<210> SEQ ID NO 25
<211> LENGTH: 8
<212> TYPE: PRT
<213> ORGANISM: Artificial
<220> FEATURE:
<223> OTHER INFORMATION: Novel Sequence

<400> SEQUENCE: 25

Lys Thr Lys Gly Ser Gly Asn Thr
1               5
```

```
<210> SEQ ID NO 26
<211> LENGTH: 4
<212> TYPE: PRT
<213> ORGANISM: Artificial
<220> FEATURE:
<223> OTHER INFORMATION: Novel Sequence

<400> SEQUENCE: 26

Pro Gly Gln Asp
1

<210> SEQ ID NO 27
<211> LENGTH: 5
<212> TYPE: PRT
<213> ORGANISM: Artificial
<220> FEATURE:
<223> OTHER INFORMATION: Novel Sequence

<400> SEQUENCE: 27

Pro Gly Gln Asp Cys
1               5

<210> SEQ ID NO 28
<211> LENGTH: 5
<212> TYPE: PRT
<213> ORGANISM: Artificial
<220> FEATURE:
<223> OTHER INFORMATION: Novel Sequence

<400> SEQUENCE: 28

Gln Pro Gly Gln Asp
1               5

<210> SEQ ID NO 29
<211> LENGTH: 6
<212> TYPE: PRT
<213> ORGANISM: Artificial
<220> FEATURE:
<223> OTHER INFORMATION: Novel Sequence

<400> SEQUENCE: 29

Pro Gly Gln Asp Cys Arg
1               5

<210> SEQ ID NO 30
<211> LENGTH: 7
<212> TYPE: PRT
<213> ORGANISM: Artificial
<220> FEATURE:
<223> OTHER INFORMATION: Novel Sequence

<400> SEQUENCE: 30

Gln Pro Gly Gln Asp Cys Arg
1               5

<210> SEQ ID NO 31
<211> LENGTH: 5
<212> TYPE: PRT
<213> ORGANISM: Artificial
<220> FEATURE:
<223> OTHER INFORMATION: Novel Sequence

<400> SEQUENCE: 31

Gly Gln Asp Cys Arg
1               5
```

<210> SEQ ID NO 32
<211> LENGTH: 9
<212> TYPE: PRT
<213> ORGANISM: Artificial
<220> FEATURE:
<223> OTHER INFORMATION: Novel Sequence

<400> SEQUENCE: 32

Leu Ala Ala Phe Pro Glu Asp Arg Ser
1               5

<210> SEQ ID NO 33
<211> LENGTH: 321
<212> TYPE: DNA
<213> ORGANISM: Artificial
<220> FEATURE:
<223> OTHER INFORMATION: Novel Sequence

<400> SEQUENCE: 33

```
gatatccaga cgacacagac tacatcctcc cgttctgcct ctctgggaga cagagtcacc      60
atcagttgca gggcaggtca ggacattagt aattatttaa actggtatca gcagaaacca     120
gatggaactg ttaagctcct gatctactac acatcaagat acactcagg  agtcccatca     180 aggttcagtg gcagtgggtc tggaacagat tattctctca ccattagcaa cctggagcaa     240
gaagatattg ccacttactt ttgccaacag ggtcatacgc ttccgtggac gttcggtgga     300
ggcaccaagc tggaaatcaa a                                               321
```

<210> SEQ ID NO 34
<211> LENGTH: 107
<212> TYPE: PRT
<213> ORGANISM: Artificial
<220> FEATURE:
<223> OTHER INFORMATION: Novel Sequence

<400> SEQUENCE: 34

Asp Ile Gln Thr Thr Gln Thr Thr Ser Ser Leu Ser Ala Ser Leu Gly
1               5                   10                  15

Asp Arg Val Thr Ile Ser Cys Arg Ala Gly Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly His Thr Leu Pro Trp
                85                  90                  95

Thr Phe Gly Gly Gly Thr Lys Leu Glu Ile Lys
            100                 105

<210> SEQ ID NO 35
<211> LENGTH: 363
<212> TYPE: DNA
<213> ORGANISM: Artificial
<220> FEATURE:
<223> OTHER INFORMATION: Novel Sequence

<400> SEQUENCE: 35

```
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttccaggaa acaaactgga gtggatgggc tacataagat acagtggtag tactagctac     180
```

```
aatccatctc tcaaaagtcg aatctctatc actcgagaca catccaagaa ccagttcttc      240
ctgcagttga attctgtgac tactgaggac acagccacat attactgtgc aagagattgg      300
ccgcgaccga gctactggta cttcgatgtc tggggcgcag ggaccacggt caccgtctcc      360
tca                                                                    363
```

<210> SEQ ID NO 36
<211> LENGTH: 121
<212> TYPE: PRT
<213> ORGANISM: Artificial
<220> FEATURE:
<223> OTHER INFORMATION: Novel Sequence

<400> SEQUENCE: 36

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Arg Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Asp Trp Pro Arg Pro Ser Tyr Trp Tyr Phe Asp Val Trp Gly
            100                 105                 110

Ala Gly Thr Thr Val Thr Val Ser Ser
        115                 120
```

<210> SEQ ID NO 37
<211> LENGTH: 360
<212> TYPE: DNA
<213> ORGANISM: Artificial
<220> FEATURE:
<223> OTHER INFORMATION: Novel Sequence

<400> SEQUENCE: 37

```
caggtccaac tgcagcagtc cggacctgag ctggtgaagc cggggacttc agtgaggatt      60
tcctgcgagg cttctggcta caccttcaca agctactata cactgggtga aacagagg       120 cctggacagg gacttgagtg gattggatgt atttatcctg gaaatgtcaa tactaactat      180
aatgagaagt tcaaggacaa ggccacactg attgtagaca catcctccaa cactgcctac      240
atgcagctca gcagaatgac ctctgaggac tctgcggtct atttctgtac aagatcacac      300
tacggcctcg actggaactt cgatgtctgg ggcgcaggga ccacggtcac cgtctcctca      360
```

<210> SEQ ID NO 38
<211> LENGTH: 120
<212> TYPE: PRT
<213> ORGANISM: Artificial
<220> FEATURE:
<223> OTHER INFORMATION: Novel Sequence

<400> SEQUENCE: 38

```
Gln Val Gln Leu Gln Gln Ser Gly Pro Glu Leu Val Lys Pro Gly Thr
1               5                   10                  15

Ser Val Arg Ile Ser Cys Glu Ala Ser Gly Tyr Thr Phe Thr Ser Tyr
            20                  25                  30
```

Tyr Ile His Trp Val Lys Gln Arg Pro Gly Gln Gly Leu Glu Trp Ile
            35                  40                  45

Gly Cys Ile Tyr Pro Gly Asn Val Asn Thr Asn Tyr Asn Glu Lys Phe
 50                  55                  60

Lys Asp Lys Ala Thr Leu Ile Val Asp Thr Ser Asn Thr Ala Tyr
 65                  70                  75                  80

Met Gln Leu Ser Arg Met Thr Ser Glu Asp Ser Ala Val Tyr Phe Cys
                85                  90                  95

Thr Arg Ser His Tyr Gly Leu Asp Trp Asn Phe Asp Val Trp Gly Ala
            100                 105                 110

Gly Thr Thr Val Thr Val Ser Ser
            115                 120

<210> SEQ ID NO 39
<211> LENGTH: 321
<212> TYPE: DNA
<213> ORGANISM: Artificial
<220> FEATURE:
<223> OTHER INFORMATION: Novel Sequence

<400> SEQUENCE: 39
gacatccaga tgaaccagtc tccatccagt ctgtctgcat cccttggaga cacaattacc      60
atcacttgcc atgccagtca aacatttat gtttggttaa actggtacca gcagaaacca    120
ggaaatattc ctaaactctt gatctataag gcttccaacc tgcacacagg cgtcccatca    180
aggtttagtg gcagtggatc tggaacaggc ttcacattaa ccatcagcag cctgcagcct    240
gaagacattg ccacttacta ctgtcaacag ggtcaaactt atccgtacac gttcggaggg    300
gggaccaagc tggaaataaa a                                              321

<210> SEQ ID NO 40
<211> LENGTH: 107
<212> TYPE: PRT
<213> ORGANISM: Artificial
<220> FEATURE:
<223> OTHER INFORMATION: Novel Sequence

<400> SEQUENCE: 40

Asp Ile Gln Met Asn Gln Ser Pro Ser Ser Leu Ser Ala Ser Leu Gly
 1               5                  10                  15

Asp Thr Ile Thr Ile Thr Cys His Ala Ser Gln Asn Ile Tyr Val Trp
            20                  25                  30

Leu Asn Trp Tyr Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Thr Tyr Pro Tyr
                85                  90                  95

Thr Phe Gly Gly Gly Thr Lys Leu Glu Ile Lys
            100                 105

<210> SEQ ID NO 41
<211> LENGTH: 15
<212> TYPE: PRT
<213> ORGANISM: Artificial
<220> FEATURE:
<223> OTHER INFORMATION: Novel Sequence

```
<400> SEQUENCE: 41

Gly Asn Tyr Ser Gln Gln Leu Gln Val Tyr Ser Lys Thr Gly Phe
1               5                   10                  15

<210> SEQ ID NO 42
<211> LENGTH: 15
<212> TYPE: PRT
<213> ORGANISM: Artificial
<220> FEATURE:
<223> OTHER INFORMATION: Novel Sequence

<400> SEQUENCE: 42

Tyr Met Met Gly Asn Glu Leu Thr Phe Leu Asp Asp Ser Ile Cys
1               5                   10                  15

<210> SEQ ID NO 43
<211> LENGTH: 15
<212> TYPE: PRT
<213> ORGANISM: Artificial
<220> FEATURE:
<223> OTHER INFORMATION: Novel Sequence

<400> SEQUENCE: 43

Lys Thr Lys Gly Ser Gly Asn Thr Val Ser Ile Lys Ser Leu Lys
1               5                   10                  15

<210> SEQ ID NO 44
<211> LENGTH: 16
<212> TYPE: PRT
<213> ORGANISM: Artificial
<220> FEATURE:
<223> OTHER INFORMATION: Novel Sequence

<400> SEQUENCE: 44

Leu Ala Ala Phe Pro Glu Asp Arg Ser Gln Pro Gly Gln Asp Cys Arg
1               5                   10                  15

<210> SEQ ID NO 45
<211> LENGTH: 220
<212> TYPE: PRT
<213> ORGANISM: Homo sapien

<400> SEQUENCE: 45

Met Leu Arg Leu Leu Ala Leu Asn Leu Phe Pro Ser Ile Gln Val
1               5                   10                  15

Thr Gly Asn Lys Ile Leu Lys Val Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
```

```
                   145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 46
<211> LENGTH: 222
<212> TYPE: PRT
<213> ORGANISM: Homo sapien

<400> SEQUENCE: 46

Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Lys Met Leu Lys Lys Arg
            180                 185                 190

Ser Pro Leu Thr Thr Gly Val Tyr Val Lys Met Pro Pro Thr Glu Pro
        195                 200                 205

Glu Cys Glu Lys Gln Phe Gln Pro Tyr Phe Ile Pro Ile Asn
    210                 215                 220

<210> SEQ ID NO 47
<211> LENGTH: 199
<212> TYPE: PRT
<213> ORGANISM: Homo sapien

<400> SEQUENCE: 47

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
                20                  25                  30

Phe His Asn Gly Gly Val Gln Ile Leu Cys Lys Tyr Pro Asp Ile Val
            35                  40                  45
```

```
Gln Gln Phe Lys Met Gln Leu Leu Lys Gly Gly Gln Ile Leu Cys Asp
 50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                 85                  90                  95

Tyr Asn Leu Asp His Ser His Ala Asn Tyr Tyr Phe Cys Asn Leu Ser
                100                 105                 110

Ile Phe Asp Pro Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
        130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
            195

<210> SEQ ID NO 48
<211> LENGTH: 288
<212> TYPE: PRT
<213> ORGANISM: Homo sapien

<400> SEQUENCE: 48

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Phe Pro Ala Leu Leu Val Val Thr Glu Gly Asp
             35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205
```

Leu Lys Glu Asp Pro Ser Ala Val Pro Val Phe Ser Val Asp Tyr Gly
         210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 49
<211> LENGTH: 107
<212> TYPE: PRT
<213> ORGANISM: Artificial
<220> FEATURE:
<223> OTHER INFORMATION: Novel Sequence

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105

<210> SEQ ID NO 50
<211> LENGTH: 120
<212> TYPE: PRT
<213> ORGANISM: Artificial
<220> FEATURE:
<223> OTHER INFORMATION: Novel Sequence

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
        115                 120